United States Patent
Scales

(10) Patent No.: US 10,639,342 B2
(45) Date of Patent: May 5, 2020

(54) ANTI-OXIDANT PROPERTIES OF CORNUS SERICEA

(71) Applicant: RED DOG ENTERPRISES LTD., Swan River (CA)

(72) Inventor: Robert Scales, Swan River (CA)

(*) Notice: Subject to any disclaimer, the term of this patent is extended or adjusted under 35 U.S.C. 154(b) by 242 days.

(21) Appl. No.: 14/396,540

(22) PCT Filed: Apr. 22, 2013

(86) PCT No.: PCT/CA2013/050312
§ 371 (c)(1),
(2) Date: Oct. 23, 2014

(87) PCT Pub. No.: WO2013/159226
PCT Pub. Date: Oct. 31, 2013

(65) Prior Publication Data
US 2015/0093460 A1 Apr. 2, 2015

Related U.S. Application Data

(60) Provisional application No. 61/683,140, filed on Aug. 14, 2012.

(51) Int. Cl.
*A61K 36/40* (2006.01)
*A23K 10/30* (2016.01)
*A23K 20/10* (2016.01)

(52) U.S. Cl.
CPC .............. *A61K 36/40* (2013.01); *A23K 10/30* (2016.05); *A23K 20/10* (2016.05); *A61K 2236/00* (2013.01)

(58) Field of Classification Search
None
See application file for complete search history.

(56) References Cited

FOREIGN PATENT DOCUMENTS

| JP | 2003342190 A | * | 12/2003 |
| KR | 20040067738 A | * | 7/2004 |
| KR | 20100021040 A | * | 2/2010 |

OTHER PUBLICATIONS

NetDoctor. Treatments for bacterial infections (antibiotics). Retrieved from the Internet on: Jan. 18, 2017. Retrieved from the Internet: <URL: http://www.netdoctor.co.uk/medicines/infections/a25910/treatments-for-bacterial-infections-antibiotics/>.*
Merck. Merck Manual Consumer Version: Overview of viral infections. Retrieved from the Internet on: Jan. 18, 2017. Retrieved from the Internet: <URL: https://www.merckmanuals.com/home/infections/viral-infections/overview-of-viral-infections>.*
Mayo clinic. "Diseases and conditions: Gout". Retrieved from the Internet on: Jan. 18, 2017. Retrieved from the Internet: <URL: https://www.nhlbi.nih.gov/health/health-topics/topics/copd/treatment>.*
NIH: National Heart, Lung and Blood Institute. Retrieved from the Internet on: Jan. 18, 2017. Retrieved from the Internet: <https://www.nhlbi.nih.gov/health/health-topics/topics/copd/treatment>.*
BeyondDisease (BeyondDisease.com). Internet date: Aug. 13, 2015 [Retrieved from the Internet on: Jan. 18, 2017]. Retrieved from: <URL:http://www.beyonddisease.com/top-ways-to-increase-height-and-grow-taller>.*
Eowyndbh. Web Publication Date: Sep. 28, 2011 [Retrived from the Internet on: Jan. 18, 2017]. Retrieved from: <URL:https://keys2liberty.wordpress.com/tag/red-osier/>.*
American Psychologist (American psychological association). Criteria for Evaluating Treatment Guidelines. American Psychologist (Dec. 2002), 1052-1053.*
"Cornus sericea". Internet Archive Date: Dec. 18, 2008. Retrieved from the internet on: <http://web.archive.org/web/20081218103632/http://www.fs.fed.us/database/feis/plants/shrub/corser/all.html>.*
Moerman, D. Native American Food Plants: An Ethnobotanical dictionary. p. 90 (Year: 2010).*
Eowyndbh. "Dogwood" from "Wild Edible and Medicinal Plants #1/4 Common Reed, Dogwood, Purpleosier Willow, Pinedrops". Internet posting date: Sep. 28, 2011 [Retrieved from the Internet on: Sep. 3, 2018]. Retrieved from: <URL: https://keys2liberty.wordpress.com/tag/red-osier/>. (Year: 2011).*
Allrefer.com. Web Archive Date: Apr. 28, 2005. [Retrieved from the Internet on: Sep. 3, 2018]. Retrieved from: <URL: https://web.archive.org/web/20050428200355/http://reference.allrefer.com/wildlife-plants-aninnals/plants/tree/corser/value-use.html:>. (Year: 2005).*
Kharal et al. "Quinine is bactericidal". J Pak Med Assoc. vol. 59, No. 4, Apr. 2009. pp. 208-211. (Year: 2009).*
Gennaro, E. Ed. Chapter 84: Solutions, Emulsions, Suspensions, and Extractives Nairn, JG. "Solutions, Emulsions, Suspensions, and Extractives" from Remington's Pharmaceutical Science: 17th Ed. Joseph P. Remington. Mack Publishing Co., 1985. pp. 1492, 1513, 1516-1517 (Year: 1985).*
D.E. Moerman, Passage Native American Medicinal Plants: An Ethnobotanical Dictionary, Timber Press 2009, p. 154-159, XP008178416.
M.A. Sarvary et al., Biological Comtrol 2010, 55 (2),p. 110-117, XP027266201.
L. Cheryl et al., Journal of Ethnobiology and Ethnomedicine 2007, 3 (1), p. 1-22, XP021025895.
G. J. King et al., Journal of Chromatagraphy 1987, 407 (1), p. 377-383, XP026554510.
O. Bjoroy et al., Phytochemistry 2007, 68 (5), p. 640-645, XP005895968.
R. Zach et al., Canadian Journal of Zoology/Journal Canadien de Zoologie 1982, 60 (6), p. 1300-1304, XP008178382.
L.R.H. Mohlenbrook, Plant Guide Redosier Dogwool, *Serecea cornus*, USD NRCS, 2002, XP055234255.
Stankovic, M. and Topuzovic, M. In vitro antioxidant activity of extracts from leaves and fruits of common dogwood (*Cornus sanguinea* L.) Acta Botanica Gallica, Mar. 2012 Vol.
Tiwari p et al Phtochemical screening and extract, A Review Internationale Pharmaceutica Sciencia Mar. 2011 vol. 1 Issue 1 pp. 98-106.

* cited by examiner

*Primary Examiner* — Amy L Clark
(74) *Attorney, Agent, or Firm* — Michael R. Williams; Ryan W. Dupuis; Ade & Company Inc.

(57) ABSTRACT

Red Osier Dogwood can be fed to domesticated animals such as livestock as part of a feeding regimen in place of silage. The Red Osier Dogwood results in increased growth compared to a control fed a regular diet. The Red Osier Dogwood is rich in antioxidants such as rutin, gallic acid, ellagic acid, quercetin and tyrosol. Extracts from Red Osier Dogwood can be used in the preparation of medicaments for the administration to animals, including humans.

7 Claims, 2 Drawing Sheets

Figure 1. ORAC Assay - Dogwood Samples 20100930
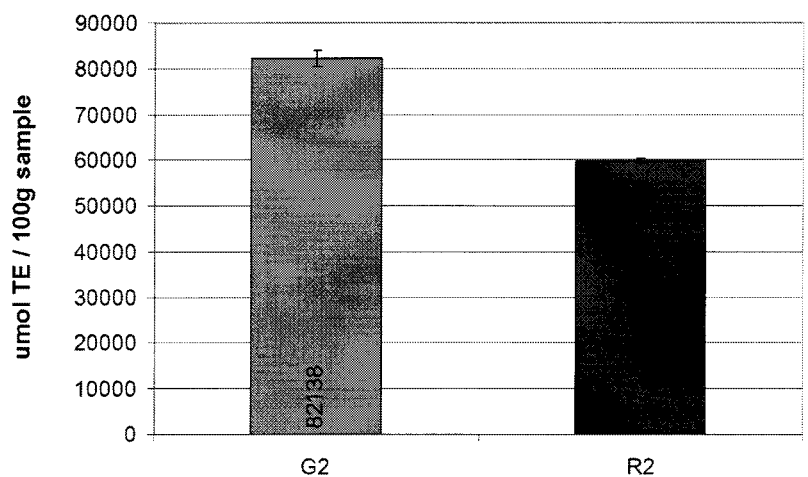
Figure 2. ORAC Assay - Dogwood Samples
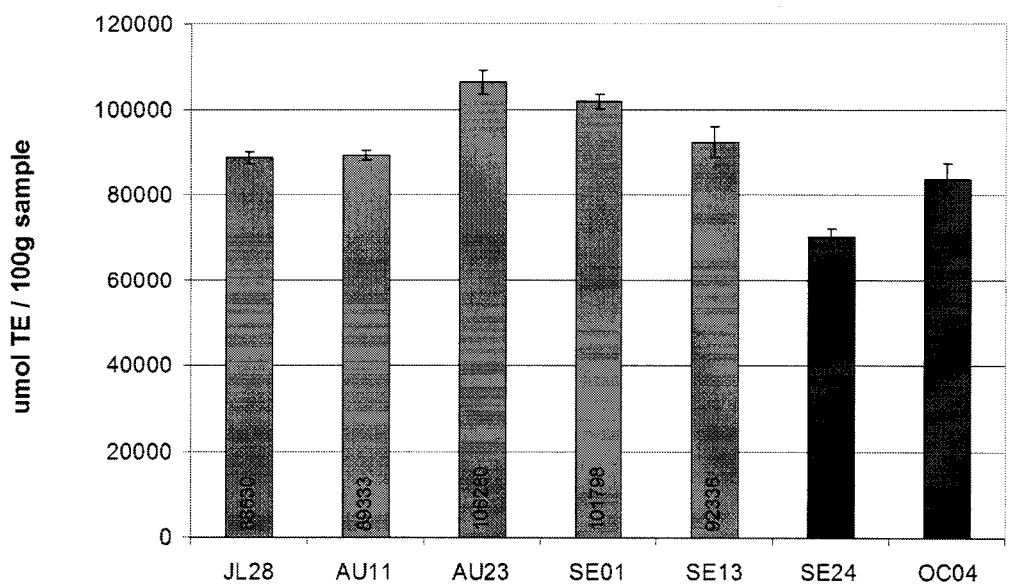

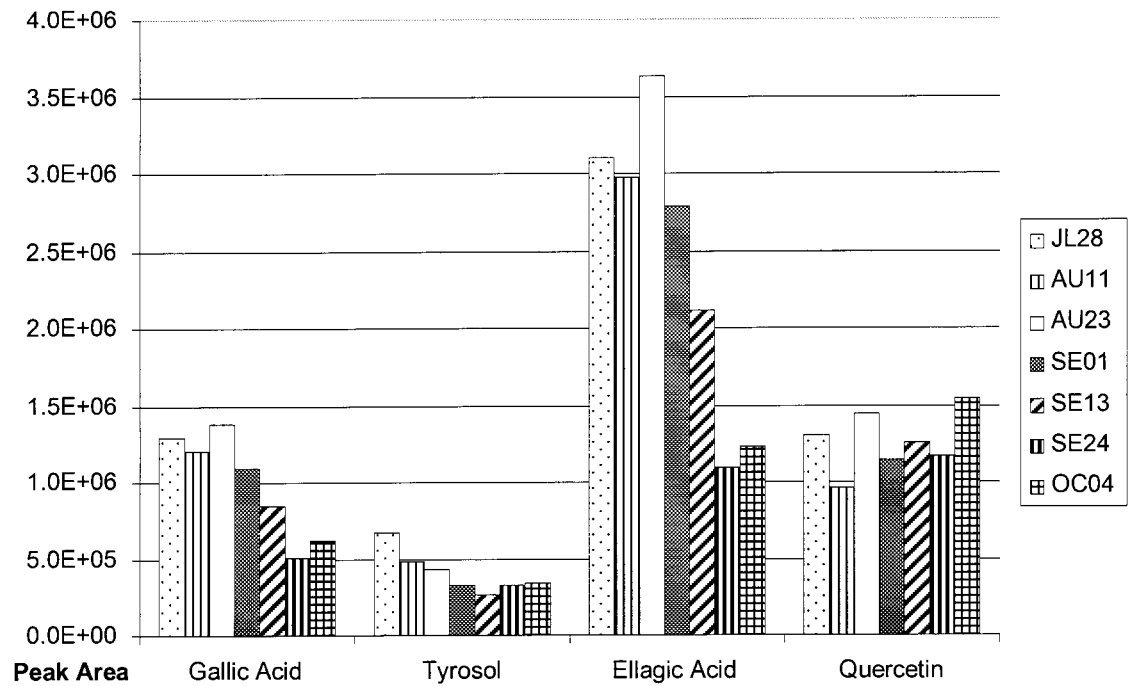
Figure 3. UPLC Analysis of Dogwood After Acid Hydrolysis
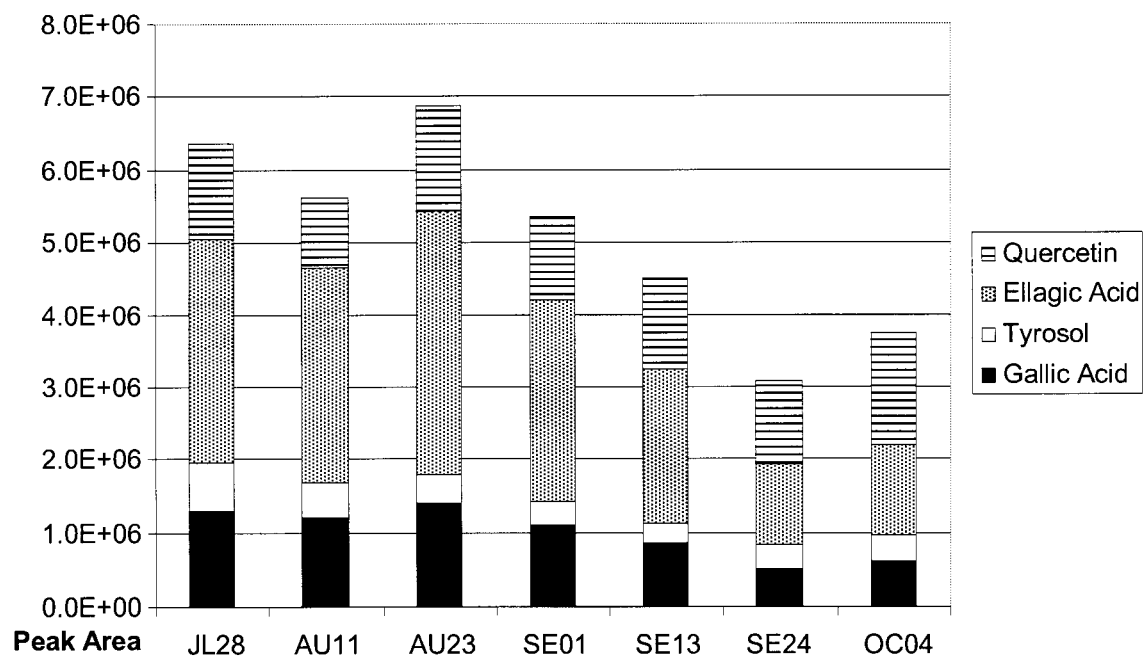
Figure 4. UPLC Analysis of Dogwood After Acid Hydrolysis

ANTI-OXIDANT PROPERTIES OF CORNUS SERICEA

PRIOR APPLICATION INFORMATION

The instant application claims the benefit of U.S. Provisional Application U.S. Ser. No. 61/638,140, filed Apr. 25, 2012.

BACKGROUND OF THE INVENTION

Red-Osier Dogwood (*Cornus sericea* syn. *C. stolonifera, Swida sericea*), also known as Red Willow, Kinnikinnick, Redstem Dogwood, Redtwig Dogwood, Red-rood, American Dogwood, Creek Dogwood and Western Dogwood, grows on marginal land and is abundant in low wetlands, pasture land and areas where crops and forages do not grow well. Red-Osier Dogwood can tolerate flooding and can survive long periods with its roots below water, but is also drought tolerant.

Red Osier Dogwood is a popular ornamental shrub that is used for waterway bank erosion protection because of its root system.

This shrub is found across Northern and Western North America and across a range of dry to wet forest habitats and does well on poorly drained soils. It is a hardy plant which can be propagated by seed after cold stratification or by cuttings. Cuttings of red-osier dogwood will root with sufficient moisture. Dogwood can also be seeded using conventional methods.

Once established, Red-Osier Dogwood can be harvested annually. Harvest can be done year round if conditions permit. In some lower areas, freeze up may have to occur prior to harvesting.

The seeds themselves take up to sixty days to germinate. They grow to a height of up to six inches the first year. They will reach a height of approximately 2 feet in year 2.

The Wikipedia entry for Red Osier Dogwood states that "some Plateau Indian tribes ate the berries to treat colds and slow bleeding". It further states that "the red osier dogwood was also used by the Lakota and other North Americans as 'traditional tobacco', either by itself or in a mixture with other plant materials".

Red-osier dogwood provides a valuable cover for birds and many small animals. It is also used for food and cover by deer, elk, moose, rabbits, and grouse to name a few. In the winter months, the plant is often consumed by wild animals such as moose, deer and elk.

However, to the inventor's knowledge, Red Osier Dogwood has not been used to replace silage in the diet of livestock nor have the antioxidant properties of the plant been extracted and/or exploited.

SUMMARY OF THE INVENTION

According to a first aspect of the invention, there is provided a method of promoting growth or improving growth in an animal comprising feeding an animal an effective amount of immature Red Osier Dogwood plant derived material.

As discussed herein, the inventor has discovered growth conditions to maximize production of certain anti-oxidants by the plant. Consequently, powders, for example, natural powders prepared by grinding the plant material as discussed below, can be used as a feed supplement that replaces administration of sub-therapeutic levels of antibiotics in animals, as discussed below. These powders or antioxidants extracted therefrom can also be administered to humans or formulated for administration to humans, as discussed below.

Alternatively, the Red Osier Dogwood material may be a powder or an extract of Red Osier Dogwood plants.

According to another aspect of the invention, there is provided a method of promoting growth in an animal comprising feeding an animal an effective amount of anti-oxidants isolated Red Osier Dogwood material.

According to another aspect of the invention, there is provided a method of preparing a Red Osier Dogwood plant powder comprising:

harvesting a quantity of immature Red Osier Dogwood plant material; and grinding said immature Red Osier Dogwood plants, thereby producing a powder.

In some embodiments, the powder is used for extracting antioxidants therefrom.

Preferably, the immature Red Osier Dogwood plant material is ground to a powder such that at least 50% of the powder has a length of at least ¼ inch.

Preferably, the antioxidants are selected from the group consisting of rutin, gallic acid, ellagic acid, quercetin and tyrosol.

As discussed herein, the biologically active compounds from red osier dogwood include but are by no means limited to quercetin, gallic acid, ellagic acid, tyrosol, rutin, tannins and oligomeric proanthocyandins (OPCs).

According to another aspect of the invention, there is provided a method of preparing a Red Osier Dogwood extract comprising:

providing a quantity of immature Red Osier Dogwood plants;

grinding said immature Red Osier Dogwood plants to a powder; and extracting antioxidants from the powder using a suitable solvent.

According to a further aspect of the invention, there is provided a method of preparing a medicament for treating a disease selected from the group consisting of a viral infection, a bacterial infection, menopause symptoms, COPD and gout comprising: harvesting a quantity of immature Red Osier Dogwood plant material; grinding said immature Red Osier Dogwood plant material into a powder and formulating said powder into a medicament suitable for administration to an animal.

According to yet another aspect of the invention, there is provided a method of preparing a medicament for treating a disease selected from the group consisting of a viral infection, a bacterial infection, menopause symptoms, CORD and gout comprising: harvesting a quantity of immature Red Osier Dogwood plant material; grinding said immature Red Osier Dogwood plant material into a powder; extracting one or more biologically active agents from said powder and formulating said one or more biologically active agents into a medicament suitable for administration to an animal.

According to another aspect of the invention, there is provided a method of seeding Red Osier Dogwood plants on a field scale comprising:

collecting mature Red Osier Dogwood seeds from Red Osier Dogwood plants between July and September;

depulping the collected seeds;

cleaning the depulped seeds;

drying the cleaned and depulped seeds to a moisture content between 4-10%;

seeding the dried seeds in suitable soil to a depth of ¼ of an inch to 1 inch;

and packing the seed placement rows.

BRIEF DESCRIPTION OF THE DRAWINGS

FIG. 1 shows the results of an ORAC assay of ground dark green leaves (G2) and ground reddish brown leaves (R2).

FIG. 2 shows results of an ORAC assay of ground leaves over time (July to October).

FIG. 3 shows UPLC analysis of Dogwood after acid hydrolysis, grouped by antioxidant.

FIG. 4 shows UPLC analysis of Dogwood after acid hydrolysis grouped by date.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As discussed above, Red Osier Dogwood has an extensive root system that stops erosion and in many areas it is planted for this reason. Dogwood has a very long growing season, typically growing from April to November.

In one embodiment of the invention, there is provided a method of promoting growth or improving growth or increasing growth efficiency or increasing growth rate in an animal comprising feeding an animal an effective amount of Red Osier Dogwood material.

As will be appreciated by one of skill in the art, "an effective amount" in this context refers to an amount of the Red Osier Dogwood material that is sufficient for improved growth to be seen in a group fed the Red Osier Dogwood material according to a specific schedule or regimen compared to a control animal of similar age and condition fed a control diet.

Furthermore, "effective amount" will depend on the age and condition of the animal as well as the specific animal itself. Other factors such as the entire feeding regimen, the environmental conditions and the desired outcome will also influence "effective amount" but it is noted that determination of what constitutes an effective amount is clearly within the routine skill of one knowledgeable in the art of the animal sciences, as discussed below.

The animal may be a human.

As used herein, "improved growth" typically refers to more rapid growth or weight gain compared to an untreated control or a mock treated control. However, as discussed herein, depending on the context, "improved growth" can also refer to growth or even aging in the absence of disease or with reduced occurrences of disease and/or reduced severity thereof symptoms associated with the disease, as discussed below.

Thus, as demonstrated herein, administration of an effective amount of immature Red Osier Dogwood plants, immature Red Osier Dogwood plant materials, immature Red Osier Dogwood plant-derived powder or immature Red Osier Dogwood plant extracts to individuals in need of such treatment "improves growth", as defined above.

In some embodiments, as discussed herein, the animals are fed immature Red Osier Dogwood plants or powders or extracts prepared therefrom as part of a regular feeding regimen.

As used herein, "immature" in regards Red Osier Dogwood plants or Red Osier Dogwood plant material refers to less than four years' growth. 'Mature' means the plant has more than four years' growth and contains woody material which could be 10 years old or more. In some embodiments, the yearly growth is harvested annually (only the immature upper growth) and while the roots base will continue to get older, it will not be harvested. That is, only immature plant material is used, whether woody material is preferentially left behind or is manually separated out following harvesting of the Red Osier Dogwood plant material or if it is simply a commercial "forest" which is harvested annually or biannually such that no "mature" material is present to be harvested. Thus, "immature plants" in regards Red Osier Dogwood plants refers to "immature plant material", that is, plant growth which is 4 years or younger, preferably 3 years or younger and in some embodiments 2 years or younger.

For example, as discussed in the examples, Red Osier Dogwood plants were substituted for silage and were found to have a higher feed value than many forages and to also have higher total digestible nutrients than many high quality silages. Accordingly and as discussed herein, harvested Red Osier Dogwood plants can be fed to animals such as livestock animals as part of a feeding regimen wherein the Red Osier Dogwood plants may comprise 1-20%, 1-15%, 1-10%, 2-10%, 2-15%, 2-20%, 3-10%, 3-15%, 3-20%, 4-10%, 4-15%, 4-20%, 5-10%, 5-15% or 5-20% of the animal's daily feed.

In other embodiments, the animals are fed an extract of Red Osier Dogwood plants such that measured amounts of the respective antioxidants are delivered to the animals. In these and other embodiments, an animal is fed an effective amount of antioxidants isolated Red Osier Dogwood material, as discussed herein.

The Red Osier Dogwood powder may be prepared by: harvesting a quantity of immature Red Osier Dogwood plant material; and grinding said immature Red Osier Dogwood plant material into a powder.

The immature Red Osier Dogwood plant material may be ground such that at least 50% of the powder has a length of at least ¼ inch.

As will be appreciated by one of skill in the art, an extract may be prepared from the powder for example by drying the powder to remove water therefrom. Accordingly, in some embodiments, the term "powder" and "extract" may be used interchangeably. In other embodiments, the powder is used for further extraction of specific antioxidants therefrom, as discussed below.

As will be appreciated by one of skill in the art, conditions may be selected for the preferential extraction or isolation or enrichment of specific antioxidants or combinations thereof. In some embodiments, immature growth as defined above from Red Osier Dogwood plants is harvested and any woody portion of the plant material is removed. This immature growth is then ground to a powder.

In some embodiments, ground up material from the plant may have the woody portion removed and the material may be compressed and fed in capsules or pellets as well instead of subjecting the material to extraction.

As discussed herein, the biologically active compounds from Red Osier Dogwood include but are by no means limited to quercetin, gallic acid, ellagic acid, tyrosol, rutin, tannins and oligomeric proanthocyandins (OPCs). As discussed above, the Red Osier Dogwood immature plant material can be used for the extraction of antioxidants selected from the group consisting of rutin, gallic acid, ellagic acid, quercetin and tyrosol.

In a preferred embodiment, the solvent for antioxidant extraction is a polar solvent, for example, 80% methanol and 2% formic acid. As will be apparent to one of skill in the art, other suitable solvents for the extraction of antioxidants and OPCs may be used for routine, non-optimized extraction of antioxidants from the Red Osier Dogwood material and would be routine experimentation for one of skill in the art having knowledge of antioxidants and their properties.

Specifically, as will be appreciated by one of skill in the art, each of the anti-oxidants found in Red Osier Dogwood have different anti-oxidant properties. Accordingly, a powder or extract prepared from immature Red Osier Dogwood plant material may be used to treat a variety of diseases and conditions. As discussed herein, it has been discovered that the set of biologically active compounds in Red Osier Dogwood can treat, prevent or prophylactically treat human diseases for example infections caused by viruses or bacteria, metabolic diseases such as gout and inflammatory or autoimmune diseases.

As discussed herein, the antioxidants may be fed to weaned pigs to reduce the use of antibiotics in animals bred and raised for food production. As will be appreciated by one of skill in the art, an "effective amount" as it pertains to livestock can be determined by a variety of means without undue experimentation. For example, a number of feeding regimens may be tested and the effective amount determined from the feeding regimen or diet that either produced the most growth or the most desirable characteristics in the animal. For example, disease prevalence may be controlled at certain levels while maximum growth rate may be obtained at other levels. Thus, what exactly constitutes an "effective amount" may vary according to a number of factors, including but by no means limited to the desired outcome, the livestock species and the growth conditions/environment of the livestock.

As will be readily apparent to one of skill in the art, these antioxidants are known have beneficial health effects. Antioxidants extracted from Red Osier Dogwood may be sold individually or in combination for use by humans, for example, in pill form as health supplements in health food outlets. In other embodiments, the extract may be sold as a powdered supplement, in a form to be dissolved in a liquid for oral consumption or the like.

In some embodiments of the invention, there is provided a method of preparing a medicament comprising: harvesting a quantity of immature Red Osier Dogwood plant material; grinding said immature Red Osier Dogwood plant material into a powder and formulating said powder into a medicament suitable for administration to an animal.

In other embodiments of the invention, there is provided a method of preparing a medicament comprising: harvesting a quantity of immature Red Osier Dogwood plant material; grinding said immature Red Osier Dogwood plant material into a powder; extracting one or more biologically active agents from said powder and formulating said one or more biologically active agents into a medicament suitable for administration to an animal.

In an embodiment of the invention, there is provided a method of treating or prophylactically treating or preventing a disease selected from the group consisting of a viral infection, a bacterial infection, menopause symptoms, COPD and gout comprising administering to an individual in need of such treatment an effective amount of Red Osier Dogwood derived material.

In an embodiment of the invention, there is provided use of Red Osier Dogwood derived material for treating a disease selected from the group consisting of a viral infection, a bacterial infection, menopause symptoms, COPD (chronic obstructive pulmonary disease) and gout.

The Red Osier Dogwood derived material is preferably immature Red Osier Dogwood plant derived material as described herein, that is, immature plant material (4 or fewer years' growth, preferably 3 or fewer years' growth, more preferably 2 or fewer years' growth). The immature Red Osier Dogwood plant derived material may be an extract high in anti-oxidants and OPCs prepared as discussed above or may be a powder made of ground up Red Osier Dogwood plants.

Gout is a metabolic disease typically associated with increased uric acid pool, hyperuricemia, and episodic acute and chronic arthritis. Typically, an individual can have multiple occurrences of gout or attacks of gout within one calendar year. However, as discussed below, administration of an effective amount of the Red Osier Dogwood powder prepared as described herein has reduced the frequency of gout attacks in a number of individuals and thus can be considered to be an effective treatment or a prophylactic treatment for gout as well as being capable of preventing gout attacks.

An effective amount will accomplish at least one of the following: reduction in frequency of symptoms, longer symptom-free periods, reduction in severity of symptoms and the like.

In an embodiment of the invention, there is provided a method of improving general health in an individual in need of such treatment comprising administering to an individual in need of such treatment an effective amount of Red Osier Dogwood derived material. As discussed above, the Red Osier Dogwood plant derived material may be immature Red Osier Dogwood plant derived material and may be in the form of a powder or an extract as described above.

The improvement in general health may comprise fewer viral infections, fewer bacterial infections, improved circulation, reduced blood pressure, reduced inflammation, reduced severity of side effects associated with arthritis and reduced frequency of migraines.

As discussed in the example, Red Osier Dogwood derived powder was taken once daily by a number of individuals suffering from a variety of ailments. As discussed herein, it was discovered that daily dosages between 1 teaspoon and 1 tablespoon provided a decrease in severity of symptoms associated with or occurrences of viral infections, bacterial infections, poor circulation, high blood pressure, inflammation, arthritis, migraines, diabetes, acid reflux, gout and COPD.

In another embodiment of the invention, there is provided a method of seeding Red Osier Dogwood plants on a field scale comprising: collecting mature Red Osier Dogwood seeds from Red Osier Dogwood plants between July and September; depulping the collected seeds; cleaning the depulped seeds; drying the cleaned and depulped seeds to a moisture content between 4-10%; seeding the dried seeds in suitable soil to a depth of ¼ of an inch to 1 inch; and packing the seed placement rows.

In preferred embodiments, the seeds are collected and then placed in a water bath. Any seeds that float are removed as they are immature.

In some embodiments, the seeds are scarified or stratified prior to or after seeding.

The seeds can be depulped by any suitable means known in the art, for example, by using a commercial grade potato peeler. The depulped seeds may be stored at 5° C. prior to cleaning.

The dried seeds are seeded by any suitable means known in the art, for example by air seeder or press drill. In some embodiments, the air flow on air seeders may be reduced to prevent seed cracking.

Seeding may be done in the fall for example in October or stratified seeds that have been stored frozen may be seeded in the spring as scarification has occurred and these seeds do not have to overwinter.

Preferably, the cleaned and depulped seeds are seeded at a rate of no more than 10 pounds per acre. As will be appreciated by one of skill in the art, seeding at a higher rate will result in growth that is too dense and there will be too much competition for healthy shrubs to grow.

Preferably, areas that are extremely wet or under water in the spring are seeded in October or at near freeze up as possible so they do not germinate prior to winter. If seeded earlier, they may germinate and will freeze and not regrow in spring.

Weeds can be controlled by mowing to a height of no more than 10 inches in year 1 and mowing to no lower than 12 inches in year 2. Harvest can commence in year 3.

Preferably, harvested plants are delivered to extraction plants in bales or in some embodiments, the harvested plants may be ground up as discussed above. Specifically, plants are cut above the ground at about 8 inches above the last node so regrowth occurs. In some embodiments, woody material is removed prior to grinding. In some embodiments, the immature Red Osier Dogwood plant derived material is ground to a powder wherein greater than 50% of the particles are at least ¼ inch in length. Specifically, the inventor has surprisingly discovered that grinding too fine promotes faster spoilage.

In some embodiments, dried seeds are stored in sealed containers at −18° C. if not used for planting immediately.

As discussed above, the inventor has discovered that Red Osier Dogwood can be fed to domesticated animals such as livestock as part of a feeding regimen in place of silage, as discussed herein. Surprisingly, the Red Osier Dogwood results in increased growth compared to a control fed a regular diet.

It is noted that many livestock producers currently feed their livestock a non-therapeutic dosage of antibiotics as a growth enhancer. This practice results in greater amounts of antibiotics being introduced into the environment and the food chain than necessary which in turn results in a greater incidence of antibiotic resistant bacterial strains developing. The inventor believes that a natural growth enhancer such as Red Osier Dogwood represents an alternative to traditional antibiotics.

In North America most weaned pigs are fed low levels of antibiotics at weaning to reduce stress. This stress if unchecked will develop into scours or other diseases and result in high death losses. In a preferred embodiment of the invention, a Red Osier Dogwood extract is prepared containing these antioxidants and is fed at weaning in powder or liquid form for a period of four or more weeks at weaning time to prevent stress and reduce the level or eliminate the use of antibiotic use. As discussed above, an effective amount may depend on the breed, age, weight, condition and environment of the animal and can be determined through routine experimentation.

As discussed herein, the inventor has surprisingly found that a significant number of antioxidants can be extracted from a new feedstuff (*Corpus sericea*).

Specifically, as shown in FIGS. 3 and 4, antioxidants such as gallic acid, ellagic acid, quercetin and tyrosol were present in the dogwood leaf extracts, (also present was a fifth antioxidant rutin), after acid hydrolysis. Gallic acid and ellagic acid were present in higher amounts in leaves harvested during the warmer months of July to mid-September while there was less variability in the amount of quercetin and tyrosol over that time period, as discussed below.

Red Osier Dogwood has high levels of natural compounds such as the above-listed antioxidants which promote growth and may reduce the reliance on synthetic antibiotics, discussed above.

In some embodiments, Red Osier Dogwood is grown on field scale levels and feed to livestock in place of silage or forages as part of a feed ration or specific diet; used in the preparation of a powdered supplement; and used for the extraction of antioxidants and other bioactive compounds. The powder product or extracted products may be fed to livestock which may reduce the use of antibiotics. Alternatively, the powder or extracted antioxidants may be formulated for administration to humans using means known in the art.

The invention will now be further illustrated by way of examples; however, the invention is not necessarily limited by the examples.

Rabbit Trial

Initially, red osier dogwood was gathered on a small scale and fed to two rabbits. The one receiving the feed containing *Cornus sericea* was approximately twice as large as the control. Subsequently, a barn full of rabbits had a severe case of diarrhea prior to feeding this product. Feeding the dogwood cleared up this condition. The half of the barn which received no Red Osier Dogwood plants resulted in the rabbits dying from diarrhea.

Cattle Trial

As a result, a substantially larger amount was collected and fed to feeder cattle initially weighing 600 pounds. One group of 95 received no *Cornus sericea* while the other group of 95 was fed 2 pounds/head/day replacing some of the silage. Results showed that the group fed Red Osier Dogwood gained 0.52 pounds/head/day faster during the 38 day trial (Table 1).

Horse Trial

In a separate experiment, a horse that had a severe leg infection was also fed this product at a rate of 1.5 pounds daily for 17 days. The veterinarian's recommendation was to destroy the horse as the infection was too advanced and untreatable. However, the condition cleared up completely without the use of synthetic antibiotics.

Feeding livestock antioxidants derived from dogwood may eliminate the need for many of the synthetic antibiotics that producers rely on for medication and growth enhancement. This will eliminate the build-up of resistant bacteria and "super bugs". As well, many of these antibiotics are expelled in the urine and feces which are then applied to the land.

Identification of Anti-Oxidants and Other Biologically Active Agents

J Christopher Young, PhD (Food Research Program) with Agriculture and Agri-Food Canada in Guelph confirmed that Red Osier Dogwood shrubs contained an anti-oxidant and anti-inflammatory compound called quercitin. Quercitin exhibits both anti-inflammatory and anti-oxidant properties.

Samples were collected and sent in for an in depth analysis The analysis shows that the nutritional composition of this product is excellent and would make an ideal feed ingredient for the replacement of forages without reducing the nutrient levels in the diet. These analysis values were the lowest as the samples were collected from more mature plants. Immature red osier dogwood has much higher nutrient levels. The relative feed value is 366%, much higher than forages. The Total Digestible Nutrients (TDN) is 74.6% which is higher than high quality silages which have TDN values of approximately 60%. TDN or the energy value is similar to oats which has a TDN value of 76%.

Experiments were carried out at the University of Manitoba to determine if this plant contained antioxidant and anti-inflammatory compounds and at what levels. Results showed there were high levels of (5) separate antioxidants. As discussed above, results are shown in FIGS. 3 and 4.

Immature Dogwood Trial

Dogwood was cut between January 1 and November 15 and fed to cattle for a period of 38 days. Pen 4 received 200 lbs of dogwood per day or 2.10 lbs per head daily.

| Pen 4 | Pen 2 |
| --- | --- |
| Dogwood Fed | Control |
| 95 heifers | 95 heifers |
| Start Weight 567 lbs. | Start weight 566 lbs. |
| End Weight 661 lbs. | End Weight 640 lbs. |
| Average Daily gain 2.47 lbs/head | Average Daily gain 1.95 lbs/head |

Total increase in weight gain was 1877 lbs for the 38 days. The amount of dogwood fed to cattle was 7,600 lbs or 3.45 tonnes.

The energy (TDN) was 10.34 and 10.33 respectively and protein was 776 and 765 respectively, indicating that the nutrient composition of both diets was nearly identical, which in turn means that the increased growth was due to the higher levels of antioxidants present in the Dogwood-fed diet.

Specifically, both groups were fed 19.7% barley grain, 6.4% CO-OP 2:1™, 0.2% COOP SALT-SE™ and vitamins. However, the control group was fed 79.8% barley silage while the test group was fed 73.4% barley silage and 6.4% red osier dogwood as discussed above.

The ORAC of a sample of ground dark green leaves was compared to that of a sample of ground reddish brown leaves (FIG. 1). Results showed that the green leaf extract has a higher ORAC (by 1.4-fold) than the red leaf extract. This led to the next set of analyses to determine whether the time of harvest affected ORAC values. Samples of dogwood leaves were collected from late July to early October and ground when dried. These samples were extracted with 80% methanol and 2% formic acid and the ORAC of these extracts were determined. The results are depicted in FIG. 2 which showed that samples harvested from late August to early September had relatively higher ORAC values. The results also confirmed that green leaf extract had higher ORAC values compared to that from the red leaf. A chromatographic analysis of the samples was also performed to identify potential antioxidants that were present in the samples. FIGS. 3 and 4 showed that antioxidants such as gallic acid, ellagic acid, quercetin and tyrosol were present in the dogwood leaf extracts after acid hydrolysis. Gallic acid and ellagic acid were present in higher amounts in the plant (leaves harvested) during the warmer months of July to mid-September while there was less variability in the amount of quercetin and tyrosol. Based on these results, it can be concluded that the dogwood plant (leaves and bark from dogwood) does have antioxidant activity contributed by known antioxidant compounds.

Field Scale Red Osier Dogwood Planting

Initially, mature seeds were collected from Red Osier Dogwood plants between July and September. The seeds are depulped as soon as they are collected. In some embodiments, specialized equipment for example but by no means limited to a commercial potato peeler or other similar device is used for depulping. If necessary, the depulped seeds are stored at 5° C. prior to cleaning. The cleaned seeds are dried to a moisture content between 4 and 10%. The cleaned and depulped seeds (unsclarified) are seeded by any suitable means known in the art, for example by air seeder or press drill in October. In some embodiments, the air flow on air seeders may be reduced to prevent seed cracking. Alternatively, stratified seeds that have been stored frozen may be seeded in the spring. The cleaned and depulped seeds are seeded at a depth of ¼ to 1 inch and the seed placement rows must be packed immediately at seeding to conserve moisture.

Preferably, the cleaned and depulped seeds are seeded at a rate of no more than 10 pounds per acre.

Preferably, areas that are extremely wet or under water in the spring should be seeded in October or as near "freeze up" as possible.

Weeds can be controlled by mowing to a height of no more than 10 inches in year 1 and mowing to no lower than 12 inches in year 2. Harvest can commence in year 3.

Preferably, harvested plants are delivered to extraction plants in bales or in some embodiments, the harvested plants may be ground up as discussed above. If ground up, suitable storage methods must be used to prevent moulding.

In some embodiments, dried seeds are stored in sealed containers at −18° C. if not used for planting immediately. Can store the seeds for up to six years at this temperature.

Human Trials

One individual was administered 1 tablespoon of Red Osier Dogwood powder prepared as described above daily and reported-no sickness (influenza, colds) and no occurrences of gout during the trial period (8 months).

One individual was administered 1 teaspoon Red Osier Dogwood powder prepared as described above and a half teaspoon in ground coffee each morning—and reported no sickness, no gout and improved circulation for the duration of the trial period (11 months).

A further individual was administered 1 tablespoon powder daily and reported no occurrences of gout and improved circulation for the duration of the trial period (5 months).

Another individual was administered 1 tablespoon in ground coffee per day. And reported an improvement in general well-being over the duration of the trial period (3 months).

Yet another individual was administered 1 tablespoon powder daily and reported reduced blood pressure (returned to normal) and no recurrence of gout (which used to occur at least once per month) at the end of the trial period (9 months).

A further individual was administered 1 teaspoon of the powder daily. This individual reported reduced inflammation in elbow area and no recurrence of gout during the trial period (8 months).

Another individual was administered 1 tablespoon of powder daily and reported . . . reduced incidence of migraines and reduced severity of symptoms associated with rheumatoid arthritis for the duration of the trial period (6 months).

Still another individual was administered 1 tablespoon of powder daily and reported a reduction in the severity of symptoms associated with diabetes over the duration of the trial (6 months).

Another individual was administered 1 teaspoon of the powder daily and reported reduced migraines for the duration of the trial period (6 months).

Yet another individual was administered 1 tablespoon of the powder on a daily basis and reported a reduction in high blood pressure to normal and no gout attacks during the trial period (10 months) when previously gout attacks had occurred on average twice per month.

Another individual was administered 1 tablespoon of the powder on a daily basis and reported reduced acid reflux (no longer needed Zantac™) and improved circulation during the duration of the trial period (12 months).

Another individual was administered 1 tablespoon of the powder on a daily basis and reported reduced severity of COPD during the duration of the trial (15 months).

Yet another individual was administered 1 tablespoon of the powder on a daily basis and reported improved general well-being for the duration of the trial (6 months).

A further individual was administered 1 tablespoon of the powder daily and reported an improvement in general well-being for the duration of the trial (7 months).

Another individual was administered 1 teaspoon of the powder on a daily basis and reported no attacks of gout for the duration of the trial period (2 months).

One individual was administered 1 teaspoon of the powder per cup made into a tea for menopause-related hot flashes and experienced fewer hot flashes of reduced severity and also noted lower blood pressure throughout the trial period (7 months).

Another individual was administered 1 teaspoon of the powder twice daily as a tea and found that symptoms associated with menopause were alleviated and that the tea also acted as an appetite suppressant for the duration of the trial period (4 months).

One individual was administered 1 teaspoon of the powder daily and noted a decrease in pain associated with arthritis and also reported lower blood pressure for the duration of the trial period (4 months).

Another individual was administered two teaspoons of the powder twice daily as a tea and experienced improved immune system function, fewer oral infections and improved circulation throughout the trial period (9 months).

Another person was administered 2 teaspoons of the powder twice daily as a tea and reported a reduction in recurrences of gout throughout the trial period (3 months).

A further individual was administered 1 teaspoon of the powder daily as a tea with food and noticed reduced severity of symptoms associated with arthritis and also that the powder acted as an appetite suppressant during the trial period (6 months).

Another individual was administered 1 teaspoon of the powder daily as a tea with food and experienced lower blood pressure and noted that during the trial her thyroid was better regulated.

A further individual was administered 1 teaspoon of the powder twice daily as a tea and reported a boosted immune system during the trial period (4 months).

As can be seen, 8 separate individuals were administered the Red Osier Dogwood derived powder and reported decreased incidence of gout over significant trial periods during which time all of these individuals believe that they would normally have had several attacks of gout.

In addition, several of the participants reported an improved general feeling of well-being, indicating that the effective amount of the powder is "improving growth" as defined above.

While the preferred embodiments of the invention have been described above, it will be recognized and understood that various modifications may be made therein, and the appended claims are intended to cover all such modifications which may fall within the spirit and scope of the invention.

The invention claimed is:

1. A method of increasing weight gain in livestock animals in need thereof comprising:
   preparing a powder of Red Osier Dogwood plant parts, wherein the plant parts have less than 4 years of growth; and
   feeding an effective amount of the powder to said livestock animals as a regimen, wherein increased weight gain is observed in said livestock animals compared to livestock animals of a similar age and condition fed a control diet without the powder of Red Osier Dogwood plants.

2. The method according to claim 1, wherein the powder has been ground, wherein at least 50% of particles of the powder have a length of at least ¼ inch.

3. The method according to claim 1, wherein said powder is formulated into a medicament for administration to the livestock animals.

4. The method according to claim 1, wherein the powder is taken once daily.

5. The method according to claim 1, wherein the powder comprises 2-20% of the livestock animals' daily feed.

6. The method according to claim 1, wherein the powder is fed to the livestock animals instead of silage.

7. The method according to claim 1, wherein the powder is fed to the livestock animals as an alternative to antibiotics.

* * * * *